United States Patent [19]

Stivala

[11] 4,210,148
[45] Jul. 1, 1980

[54] RETENTION SUTURE SYSTEM

[76] Inventor: Oscar G. Stivala, 10 Whited St., Little Falls, N.Y. 13365

[21] Appl. No.: 954,221

[22] Filed: Nov. 3, 1978

[51] Int. Cl.² ............................................. A61B 17/04
[52] U.S. Cl. ................................................. 128/335
[58] Field of Search .................... 128/334 R, 335, 337

[56] References Cited

U.S. PATENT DOCUMENTS

| 2,199,025 | 4/1940 | Conn | 128/335 |
| 3,648,705 | 3/1972 | Lary | 128/335 |

FOREIGN PATENT DOCUMENTS

| 122158 | 1/1972 | Denmark | 128/335 |
| 506284 | 6/1971 | Switzerland | 128/335 |

Primary Examiner—Dalton L. Truluck
Attorney, Agent, or Firm—Bruns & Jenney

[57] ABSTRACT

A retention system for safeguarding a surgical incision to prevent rupturing of the wound during healing wherein at least one pair of elongated retaining bars of similar design and constructuion are positioned on either side of the incision. The bars are cojoined by means of retension sutures embedded beneath the skin which pass transversely across the wound. Each bar consists of a relatively rigid top plate and a complimentary lower pad that is secured to the bottom surface of the plate and which is adapted to conform to the contour of the body. One or more pair of suture holes are spaced along the longitudinal axis of each bar with the spacing between the holes being substantially equal to the width of the bar at the contact surface whereby a relatively uniform holding pressure is evenly distributed over the entire contact region when the retention sutures are tied off.

5 Claims, 4 Drawing Figures

RETENTION SUTURE SYSTEM

BACKGROUND OF THE INVENTION

This invention relates to a surgical retention system and, in particular, to apparatus for providing a uniform, evenly distributed, ligation to an incision to prevent the closure sutures from breaking and the wound from rupturing.

The most pertinent prior art known to the applicant at the time of filing this application can be found in U.S. Pat. Nos. 3,648,705 to Lary; 3,695,271 to Chodrow; 3,789,851 to LaVeen.

Relatively heavy retention sutures have been used for some time to reinforce lighter closure sutures located at the wound face and thus safeguard the incision against possible disruption as it heals. In many applications, the retention loop is passed laterally over the incision and anchored tautly below the skin on either side thereof. The sutures, in this arrangement, tend to elongate and erode into the skin at the wound face as well as causing skin necrosis and excessive scarring.

In an effort to overcome some of the noted difficulties, the retention sutures are sometimes passed over gauze pads or through rubber tubes to prevent them from being drawn directly into contact with the wound. Similarly, plastic bridges, such as those disclosed in some of the previously noted patents, have been devised which span the incision and provide a platform against which the retention sutures can act. All these prior art devices, however, require that the retention suture pass back and forth over the wound and thus prevent free access to the wound area which makes dressing or treating of the wound difficult. Furthermore, most of the bridges presently available are relatively unstable and can be easily toppled when bumped or if subjected to excessive body movement causing the entire system to fail.

Simple buttons have been used with some effectiveness as anchor points in some retention systems. The buttons are aligned on either side of the incision and suture loops passed between the buttons. Typically, two buttons on either side of the incision are joined together by means of a single loop. The two buttons are, in practice, drawn tightly against the skin when the ends of the suture loop are tied off. It has been found that retention forces in this type of system can become localized in and around the concentrated button hole region and produce excessive skin irritation and damage. The buttons, as well as many other prior art retention devices, also prevent natural perspiration from occurring thereby causing further skin irritation problems.

It is an object of the present invention to improve surgical retention systems for use in closing an incision.

A further object of the present invention is to promote healing of a surgically induced incision and thus promote greater use of this system.

Yet another object of the present invention is to minimize the extent of skin damage and irritation produced by a retention suture.

A still further object of the present invention is to provide a retention suture system which affords complete freedom of access to the retained incision.

Another object of the present invention is to distribute the holding forces of an incision retention system uniformly over a wide area to avoid the production of high localized skin pressures.

A further object of the invention is to provide a retention system employing one or more pairs of retaining bars which will allow for perspiration in the skin contact region.

A still further object of the present invention is to provide a retention suture system that is easy to implant and remove.

These and other objects of the present invention are attained by means of a retention system for maintaining closure of a surgical incision and includes at least one pair of elongated retaining bars that are of similar design and construction. Each bar consists of a relatively rigid upper plate having a complimentary sponge-like pad affixed to its bottom surface that is adapted to conform to the contour of the body. One or more pairs of suture holes are located along the longitudinal axis of the bar with the spacing between holes being substantially equal to the width of the pad at the skin contact surface. The bars are cojoined by means of retention suture loops that are embedded beneath the skin and which extend below the surface of the skin between corresponding holes in each of the bars.

BRIEF DESCRIPTION OF THE DRAWINGS

For a better understanding of these and other objects of the present invention reference is had to the following detailed description of the invention which is to be read in conjunction with the following drawings, wherein.

DESCRIPTION OF THE INVENTION

Figure 1:
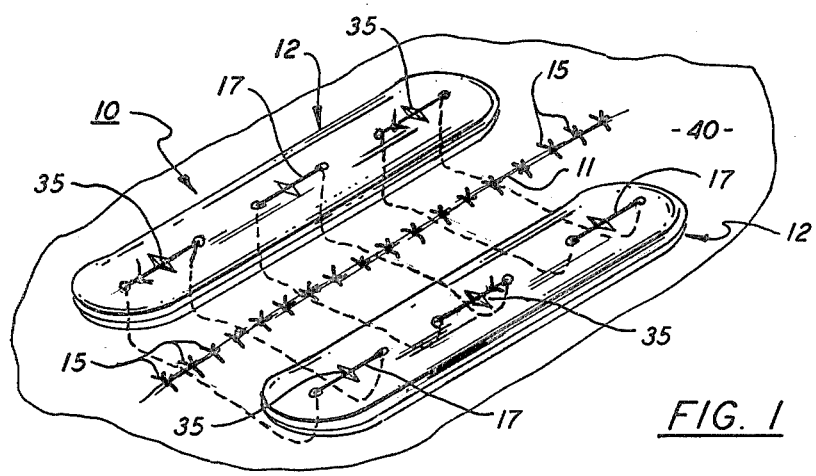
FIG. 1 is a perspective view illustrating a retention system embodying the teachings of the present invention wherein a pair of retaining bars are situated on either side of a surgically induced incision.
Figure 2:
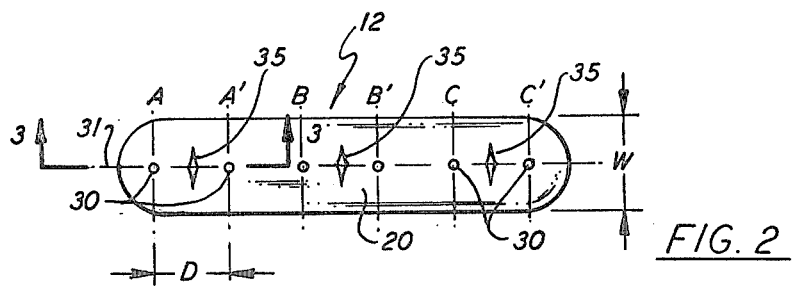
FIG. 2 is a top plan view showing one of the retaining bars used in the present system.
Figure 4:
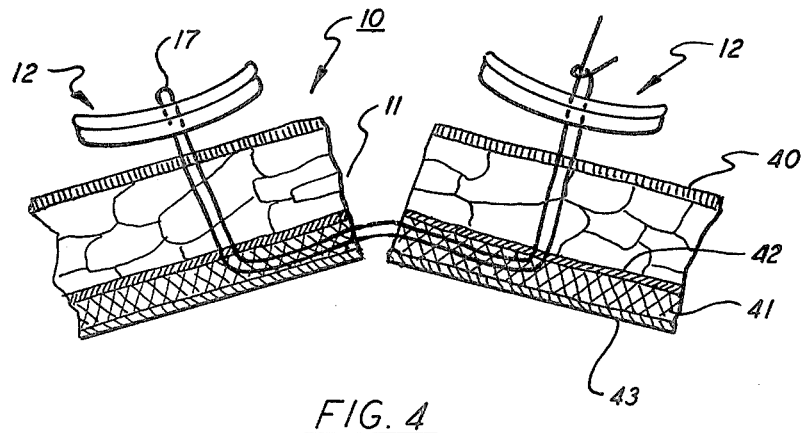
FIG. 4 is an enlarged partial front elevation in section showing the present retention system and further illustrating the manner in which suture loops are used to cojoin the bar pairs used in the system.

Referring now to the drawings, and in particular to FIGS. 1 and 4, there is shown a retention system, generally referenced 10, embodying the teachings of the present invention which is adapted for use in retaining a surgically induced wound 11 against disruption, rupture or the like as the wound is healing. The retention system contains at least one pair of elongated retaining bars 12—12 that are of similar design and construction. In the practice of the invention, the bars are strategically positioned in parallel alignment against the skin of the patient on either side of the incision. Sufficient lateral spacing is provided between the bars to allow for free and easy access to the wound as well as the closure suture loops 15 (FIG. 1) embedded in the skin at the face of the incision. As will be explained in further detail below, the bars are cojoined by means of retention suture loops 17 using conventional suturing techniques so that the sutures and the bars coact to deliver an evenly distributed retaining force for reinforcing the closure sutures 15.

Figure 3:
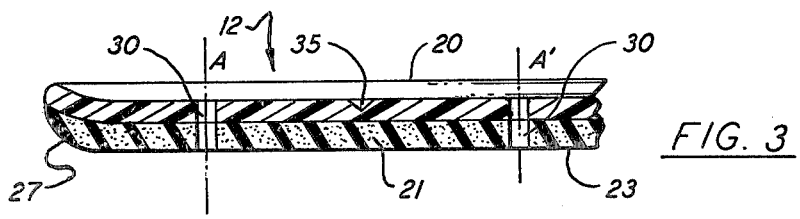
FIG. 3 is an enlarged partial section taken along lines 3—3 in FIG. 2 further illustrating the construction of the retaining bar.

With further reference to FIGS. 3 and 4, each retaining bar consists of a relatively rigid upper plate 20 and a soft, pliable lower pad 21 that is secured to the bottom surface of the plate by any suitable means. The upper plate, which is generally rectangular in form, is preferably fabricated from a plastic material which possesses sufficient resiliency to allow the plate to bend without breaking when subjected to normal body movement and pressure. The plate, however, is rigid enough to provide a secure anchor for one or more retention suture loops and serves to evenly distribute the suture forces over a relatively wide area.

The lower pad is formed of a sponge-like porous or semi-porous material that is capable of absorbing moisture. Accordingly, the pad is able to absorb perspiration from the skin while, at the same time, permitting ambient air to pass through the material. Perspiration absorbed by the pad is thus evaporated into the air and ultimately carried out of the system by means of a natural flow mechanism. In practice, the pad can be fabricated from any one of many known natural or synthetic materials having an open celled configuration.

As best illustrated in FIG. 3, a chamfer 27 is formed about the side edges of the bar whereby relatively gently sloped corners are presented to the skin of the patient. When the retention sutures are tied in assembly, the flat bottom surface 23 of the bar is drawn into conforming contact against the body. The chamfer will accommodate the deformed padding and prevent the displaced material from being gathered into tightly compressed ridges along the pad contact edges which could cause skin irritation and block the free flow of air through the material.

A series of retention suture holes 30 pass downward through the bars with the holes being centered along the bars' longitudinal axis 31. The holes are divided into pairs with each bar containing one or more hole pairs depending upon its length. Measurements of a relatively large number of adults has shown that a pair of six inch retaining bars, similar to the bars shown in the drawings, may be conveniently employed to retain a midline incision extending between the xiphoid and umbilical regions or alternatively between the umbilical and the pubic regions. Similarly, more than one pair of retaining bars of the same or of different lengths can be similarly utilized to retain a single incision. The multiple bar pair arrangement is particularly well suited where the incision passes through the umbilical region or any other bending zone. Spacing can be provided between the adjacent ends of the coaligned bars to permit relatively complete freedom of body movement within the bend region.

In the case of a six inch bar as shown, three separate pairs of suture holes are employed with the holes being equally spaced along the length of the bar. The spacing between each of the holes in a hole pair, as well as the spacing between adjacent holes in adjoining pairs, is maintained at a center distance D that is about equal to the width of the bar W as measured at the skin to pad contact surface. The centers of the two end holes contained in the bar are both located about a distance that is one-half the distance D from the two end surfaces of the bar. For explanatory purposes, the first hole pair in the series will be referred to as those holes lying upon centers A and A', the second as those holes lying upon centers B and B' and the third as those holes lying upon centers C and C'.

The retaining bars are cojoined by passing retention sutures 17 between corresponding holes in each hole pair using conventional suturing techniques. The first suture in the series is initially inserted downwardly through one of the end holes found at A in the left-hand bar as viewed in FIGS. 1 and 4. The suture is embedded below the skin 40 and passed through the tissue 41 across the incision between the fascia 42 and the peritoneum 43. The suture is brought out of the skin below the corresponding hole in the right-hand bar. The suture is brought out of the second A centered hole in the right-hand bar and inserted into the next A' centered hole in the set before being crossed back under the skin and brought out of the corresponding A' in the opposite bar. A straight run of suture is thus established along the axis of the right-hand bar which bears upon the top of the bar. The two free ends of the suture are now in a condition to be tied off thus completing one section of the retention system.

As shown in FIG. 1, the above noted procedure is repeated for the B—B' and C—C' centered hole pairs whereby three individual retention suture loops of standard length are used to tie off each of the hole pair sections. The free ends of the sutures are tied along the back of the bars as shown in FIG. 1 so that at least one straight run of suture acts against each bar along its longitudinal axis. This arrangement thus further helps to more evenly distribute the forces throughout the system. In fact, the wound can, in certain cases, be left open for draining or the like when the present system is employed because of its unique ability to uniformly distributed the holding forces.

A laterally extended notch, which is centered upon the longitudinal axis of each bar, is centered midway between each of the holes in any given pair. The notch is formed to a depth to allow the blade of a scissor to be inserted beneath the parallel run of suture passing longitudinally between the two holes in the pair. As can be seen, the suture can thus be easily severed for removal. The notches are referenced 35.

Although a six inch retaining bar is described with reference to the present invention, the invention is not necessarily limited to this particular detail and this application is intended to cover bars of any size and shape as may come within the scope of the following claims.

I claim:

1. A retaining bar for use in a retention system for safeguarding a surgical incision that includes
   an elongated plate formed of a relatively rigid material that is capable of flexing without breaking,
   a pad securely affixed to the bottom surface of the plate for contacting the skin adjacent the incision, said pad being formed of a resilient open-celled material that is capable of conforming to the contour of the skin while, at the same time, permitting air to contact the skin,
   said cojoined plate and pad having at least one suture hole pair passing downwardly therethrough with the holes being located upon the longitudinal axis of the plate and being spaced apart at a distance substantially equal to the width of said plate, and
   said plate further including laterally extended notches recessed into the top surface thereof that span the lateral axis of the plate midway between each of the holes in the hole pair, and the entire lower edge of the plate containing a gently rolled corner to prevent damaging the skin as the bar is drawn thereagainst.

2. The bar of claim 1 wherein the cojoined plate and pad contain a plurality of hole pairs and wherein the hole pairs are spaced apart a distance substantially equal to the width of the bar.

3. A retention system for safeguarding a surgical incision including at least one pair of elongated retaining bars of similar construction with the bars being parallelly aligned on either side of the incision in contact against the skin, each of said bars further including a relatively strong plastic upper plate to the bottom surface of which is securely affixed a complimentary pad formed of an open-celled resilient material that is capable of conforming to the skin contour and permitting air to reach the skin, said bars each containing a series of hole pairs spaced apart along the axis of the bar at a distance that is substantially equal to the width of the bar and also having laterally extended notches positioned between each of the holes in a hole pair, said notches being recessed into the top surface of the bar so as to span the axis thereof, and suture means for joining the bars that includes a suture being arranged to pass beneath the skin between corresponding holes of adjacent hole pairs contained in each of the bars with the suture extending axially along the top surface of the bar between each hole in a hole pair whereby a substantial uniform holding pressure is applied to the skin across the entire area of the bar when the sutures are tied off.

4. The retention system of claim 3 wherein the plate of each bar further includes a rounded lower edge extending about the entire periphery thereof to prevent damaging the skin when the sutures are tied off.

5. The retention system of claim 4 wherein the ends of each bar are semicircular in form.

* * * * *